United States Patent [19]

Sitzmann

[11] Patent Number: 4,777,258

[45] Date of Patent: Oct. 11, 1988

[54] METHOD FOR PREPARING 2,5-DIPCRYL-1,3,4-OXADIAZOLE

[75] Inventor: Michael E. Sitzmann, Adelphi, Md.

[73] Assignee: The United States of America as represented by the Secretary of the Navy, Washington, D.C.

[21] Appl. No.: 43,262

[22] Filed: Apr. 23, 1987

[51] Int. Cl.$^4$ .......................................... C07D 271/10
[52] U.S. Cl. .................................................. 548/145
[58] Field of Search ........................................ 548/145

[56] References Cited

FOREIGN PATENT DOCUMENTS 892767  3/1962  United Kingdom ................ 548/145

OTHER PUBLICATIONS

Dacons, J. Het. Chem., 14, 1151 (1977).

*Primary Examiner*—Robert Gerstl
*Attorney, Agent, or Firm*—Kenneth E. Walden; Roger D. Johnson

[57] ABSTRACT

A process for preparing 2,5-dipicryl-1,3,4-oxadiazole by reacting N,N'-bis(2,4,6-trinitrobenzoyl)hydrazine with phosphorus pentachloride in a chlorinated hydrocarbon which is 1,2-dichloroethane, 1,1,1-trichloroethane, 1,1,2-trichloroethane, 1,1,2-trichloroethylene, or a mixture thereof at a temperature of from 70° C. to the reflux temperature.

6 Claims, No Drawings

METHOD FOR PREPARING 2,5-DIPCRYL-1,3,4-OXADIAZOLE

BACKGROUND OF THE INVENTION

This invention relates to polynitro aromatic compounds and more particularly to thermally stable polynitro aromatic explosive compounds.

2,5-Dipicryl-1,3,4-oxadiazole is thermally stable in the vicinity of 260° C. and has an impact sensitivity of 20 cm as measured by an ERL machine (2.5 Kg weight, type 12 tools on sandpaper). This combination of impact sensitivity and thermal stability is unique. Comparing 2,5-dipicryl-1,3,4-oxadiazole with its nearest competitors (see table 1) shows that 2,2',4,4',6,6'-hexanitrostilbene (HNS) and 2,2',2'',4,4',4'',6,6',6''-nonanitroterphenyl (NONA) have similar thermal stabilities but are not as impact sensitive. 2,5-dipicryl-3,4-dinitrofuran has a similar impact sensitivity to 2,5-dipicryl-1,3,4-oxadiazole but it is not as thermally stable.

Short pulse shock tests (exploding foil) on 2,5-dipicryl-1,3,4-oxadiazole showed that it has a shock sensitivity similar to that of pentaerythritol tetranitrate (PETN) (see Table 2). Moreover, the tests also showed that 2,5-dipicryl-1,3,4-oxadiazole has a very sharp threshold of initiation (that is, it always detonates when stimulated at the required energy level but does not detonate below this level). This is a very desirable property for an initiating explosive.

TABLE 1

| Explosive | Thermal Stability at 260° C. cc/g/hr. (2 hr.) | Impact Sensitivity (cm) |
| --- | --- | --- |
| 2,5-dipicryl-1,3,4-oxadiazole (recrystallized) | 0.6 | 20 |
| NONA (recrystallized) | 0.5 | 39 |
| HNS (recrystallized) | 0.5 | 45 |
| HNS (Grade I) (not recrystallized) | 1.7 | 40 |
| 2,5-dipicryl-3,4-dinitrofuran (recrystallized) | 0.8 at 230° C. | 23 |

TABLE 2

| | SHORT PULSE SHOCK TEST | | |
| --- | --- | --- | --- |
| Explosive | Threshold Flyer Velocity | Density | Cons. Pressure |
| PETN, Class 2 | 2.21 km/sec | 1.50 | 103.4 MPa |
| 2,5-dipicryl-1,3,4-oxadiazole | 2.33 km/sec | 1.61 | 103.4 MPa |

Because of its high thermal stability and impact sensitivity, 2,5-dipicryl-1,3,4-oxadiazole will be useful in slapper detonators, explosive logic systems, detonation transfer compositions, and electric bridge wire explosives. Moreover, it promises to be useful as a thermally stable initiating explosive for use in perforators for deep oil and gas wells. All that is needed is an efficient, economical process for preparing pure 2,5-dipicryl-1,3,4-oxadiazole.

Sharmin, G. P.; Buzykin, B. I.; and Fassakhov, R. Kh. in U.S.S.R. 233,671 (Cl. C07d), 24 Dec. 1965, Appl. 09 Oct. 1967 (C.A. 70:115162) and in Khimiya Geterotsiklicheskikh Soedinenii, No. 6, pp. 741-743, June, 1977 (C.A. 87:184435) disclose the preparation of 2,5-dipicryl-1,3,4-oxadiazole by refluxing 2 mmol. (1.20 g) of N,N'-bis(2,4,6-trinitrobenzoyl)hydrazine in 100 ml of $POCl_3$ for 20 hours. The large quantity of $POCl_3$ required for this procedure makes scale up dangerous and impractical. The long reaction (reflux) time required, the poor yields and impurity of product further make this process impractical for commercial production.

Dacons, Joseph C.; and Sitzmann, Michael E., *Journal of Heterocylic Chemistry*, 14, 1151–5 (1977) disclose the cyclization of N,N'-bis(2,4,6-trinitrobenzoyl)hydrazine with $PCl_5$ in nitrobenzene to produce 2,5-dipicryl-1,3,4-oxadiazole in yields of 30–35 percent. Separation of the product 2,5-dipicryl-1,3,4-oxadiazole from nitrobenzene (b.p. 210° C.) is very difficult. The nitrobenzene is removed either by steam distillation or by pouring the nitrobenzene reaction mixture into a second solvent (e.g., methanol) in which 2,5-dipicryl-1,3,4-oxadiazole is much less soluble. However, combining the nitrobenzene with a second solvent makes it quite difficult to recycle the nitrobenzene for further use in the process. In summary, this procedure would be difficult and expensive to scale up for commercial production.

It would therefore be desirable to provide a relatively simple, low cost method of producing 2,5-dipicryl-1,3,4-oxadiazole.

SUMMARY OF THE INVENTION

Accordingly, an object of this invention is to provide a new method of preparing 2,5-dipicryl-1,3,4-oxadiazole.

Another object of this invention is to provide a less expensive method of preparing 2,5-dipicryl-1,3,4-oxadiazole.

A further object of this invention is to provide a method of producing 2,5-dipicryl-1,3,4-oxadiazole in greater yield.

Still another object of this invention is to provide a method of producing 2,5-dipicryl-1,3,4-oxadiazole in which the product is easily isolated from the reaction mixture.

These and other objects of this invention are achieved by providing:

A process for preparing 2,5-dipicryl-1,3,4-oxadiazole by reacting N,N'-bis(2,4,6-trinitrobenzoyl)hydrazine with phosphorus pentachloride in a chlorinated hydrocarbon which is 1,2-dichloroethane, 1,1,1-trichloroethane, 1,1,2-trichloroethane, 1,1,2-trichloroethylene, or a mixture thereof at a temperature of from 70° C. to the reflux temperature.

DETAILED DESCRIPTION OF THE PREFERRED EMBODIMENT

The present process uses the reaction of N,N'-bis(2,4,6-trinitrobenzoyl)hydrazine (I) with phosphorus pentachloride to produce 2,5-dipicryl-1,3,4-oxadiazole (II),

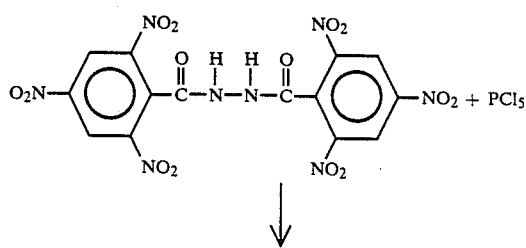

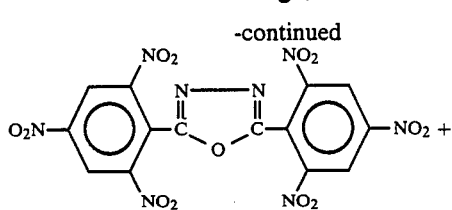

2HCl + POCl₃

The N,N'-bis(2,4,6-trinitrobenzoyl)hydrazine starting material has poor solubility in chlorinated hydrocarbons. Nevertheless, the present process achieves an increased yield and easy isolation of the product 2,5-dipicryl-1,3,4-oxadiazole by using certain chlorinated hydrocarbons as the reaction medium. Preferred among these are 1,2-dichloroethane, CH₂ClCH₂Cl; 1,1,1-trichloroethane, CCl₃CH₃; 1,1,2-trichloroethane, CHCl₂CH₂Cl; and 1,1,2-trichloroethylene, CCl₂=C.HCl. Most preferred as a reaction medium is 1,2-dichloroethane, CH₂ClCH₂Cl.

In order to hold the process costs down, the present process is preferably run at ambient (≃1 atm) pressure. In order to achieve a reasonable reaction time, the reactions should be run at 70° C. or above and preferably at 80° C. or above. As a result, chlorinated hydrocarbons with low boiling points such as methylene chloride (40° C.), chloroform (61.7° C.), chloroethane (12.3° C.), and 1,1-dichloroethane (57.3° C.) are not suitable for this process.

The process of this invention will not work with carbon tetrachloride, CCl₄, because the N,N'-bis(2,4,6-trinitrobenzoyl) hydrazine is not soluble enough in CCl₄. Similarly, highly chlorinated hydrocarbons such as 1,1,1,2-tetrachloroethane and 1,1,2,2-tetrachloroethane are preferably not used because of the very limited solubility of N,N'-bis(2,4,6-trinitrobenzoyl)hydrazine in these solvents.

Stoichiometrically one mole of phosphorus pentachloride (PCl₅) should be consumed for each mole of N,N'-bis(2,4,6-trinitrobenzoyl)hydrazine in the reaction to produce 2,5-dipicryl-1,3,4-oxadiazole. However, for better results a molar excess of PCl₅ is used. A molar ratio of PCl₅ to N,N'-bis(2,4,6-trinitrobenzoyl)hydrazine of from 1.0:1.0 to 3.0:1.0 is preferred, with from 2.0:1.0 to 2.5:1.0 being more preferred.

In theory the present process works as long as some N,N'-bis(2,4,6-trinitrobenzoyl)hydrazine starting material is present (more than zero grams per liter of chlorinated hydrocarbon). As a practical matter very low ratios of starting material to chlorinated hydrocarbon make the process inefficient. On the other hand, too much starting material adversely affects the stirrability of the reaction mixture. Therefore, preferably a concentration of from 100 to 125 grams of N,N'-bis(2,4,6-trinitrobenzoyl)hydrazine per liter of the chlorinated hydrocarbon is used; more preferably from 110 to 115 grams per liter is used.

The N,N'-bis(2,4,6-trinitrobenzoyl)hydrazine, phosphorus pentachloride, and chlorinated hydrocarbon form a slurry in the reaction vessel. The reaction temperature is preferably from 70° C. to reflux and more preferably at the reflux temperature of the chlorinated hydrocarbon solvent: CH₂ClCH₂Cl (83.5° C.), CH₃CCl₃ (74.1° C.), CH₂ClCHCl₂ (113.8° C.), and CHCl=C.Cl₂ (87° C.). The reaction mixture (or slurry) is agitated (e.g., stirred) continuously during the reaction. Two or more hours are used for the conversion of N,N'-bis(2,4,6-trinitrobenzoyl)hydrazine into 2,5-dipicryl-1,3,4-oxadiazole.

The product 2,5-dipicryl-1,3,4-oxadiazole is insoluble and is separated by filtration and then dried. The product may be further purified by recrystallization or other conventional procedures.

The chlorinated hydrocarbon filtrate contains substantial amounts of a major unknown byproduct. This byproduct has the following properties: (1) it is soluble in the chlorinated hydrocarbons, (2) it cannot be directly converted by this process to 2,5-dipicryl-1,3,4-oxadiazole, and (3) upon treatment with water it is converted back to N,N'-bis(2,4,6-trinitrobenzoyl)hydrazine starting material. Although the chlorinated hydrocarbon filtrate may be treated at this point to recover starting material and pure chlorinated hydrocarbon, it is preferably reused as the reaction medium in the 2,5-dipicryl-1,3,4-oxadiazole production step. It is preferably reused (or recycled) for from 1 to 3 times. Each time that the chlorinated hydrocarbon filtrate is used, the concentration of the major byproduct, the POCl₃, and the organic waste products increase. After the reaction has been run about four times (3 recycles) in the chlorinated hydrocarbon, the build up of these materials in the chlorinated hydrocarbon filtrate is substantial, and the recovery procedure becomes necessary.

In the recovery procedure, the chlorinated hydrocarbon filtrate is first treated with water to convert the major unknown byproduct back to N,N'-bis(2,4,6-trinitrobenzoyl)hydrazine which precipitates from solution. The N,N'-bis(2,4,6-trinitrobenzoyl)hydrazine is filtered out and recycled for use as the starting material. The chlorinated hydrocarbon phase and the water phase which remain are separated (e.g., by decanting). The water phase contains POCl₃ and other water soluble waste products and is disposed of by Environmental Protection Agency (EPA) approved means. Pure chlorinated hydrocarbon is recovered from the other phase by distillation, leaving organic waste products in the residue. The recovered chlorinated hydrocarbon is recycled for use in the process and the residue is disposed of by EPA approved means.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1

N,N'-Bis(2,4,6-trinitrobenzoyl)hydrazine

A slurry of 21.0 g (0.076 mole) of 2,4,6-trinitrobenzoyl chloride in 140 ml of methanol was vigorously stirred in a water bath at 30° C. while a solution of 7.1 g (0.12 mole) of 85% hydrazine hydrate in 35 ml of methanol was added over a 50–60 minute period. The mixture was cooled to 20° C. and the insoluble material was removed by filtration and washed with methanol until the washings were nearly colorless. The product was then washed with warm water and again with methanol to give 7.46 g (38%) of solid, mp 262° C. dec. when the melting point apparatus was preheated to 250° C. Because it is a decomposition point, the melting point varies with the rate of heating. NMR (DMSO-₆):9.30 (s) (small satellite peaks at 9.45 and 9.15); IR (KBr):3360(NH), 1730, 1710 (C=0).

EXAMPLE 2

2,5-Dipicryl-1,3,4-Oxadiazole

To 7.4 g (0.0145 mol) of N,N'-bis(2,4,6-trinitrobenzoyl)hydrazine and 65 ml of 1,2-dichloroethane stirred in a 200 ml round bottom flask was added 7.4 g (0.0355 mol) of phosphorus pentachloride. The mixture was heated to reflux temperature in an oil bath and was held at this temperature for 2.5 hrs. The mixture was cooled to room temperature and the insoluble material (3.2 g of crude 2,5-dipicryl-1,3,4-oxadiazole, mp 318° C. (dec), was removed by filtration. The crude oxadiazole was dissolved in boiling acetone (300 ml), the solution was filtered and the filtrate was concentrated by distillation until much of the acetone had been removed and an appreciable amount of crystals had formed. Methanol was slowly added with continued distillation until the distillate temperature approached 65° C. The mixture was cooled to room temperature and filtered to give 2.9 g of pure 2,5-dipicryl1,3,4-oxadiazole, mp 335° C. (vigorous decomposition). NMR (DMSO-$d_6$):9.52 (s).

To the dichloroethane filtrate (from which the crude dipicryloxadiazole was removed) was slowly added 10 ml of water. (A precipitate quickly formed after only a small amount of the water had been added.) The mixture was heated to reflux for 5 minutes, then was cooled and filtered to give 1.8 g of recovered N,N'-bis(2,4,6-trinitrobenzoyl)hydrazine. This recovered bis(trinitrobenzoyl)hydrazine (mp 277° C. dec) is a different crystal form (polymorph) than the N,N'-bis(2,4,6-trinitrobenzoyl)hydrazine [mp 262° C. dec, see Example 1] used as the original starting material. The recovered 8 bis(trinitrobenzoyl)hydrazine gave the correct elemental analysis and its NMR spectrum and thin layer chromatograms were identical to those of the original starting material, but it had a different solid phase (KBr) IR spectrum. These results are consistent with a polymorph. Treatment of the 1.8 g of recovered starting material with phosphorus pentachloride in dichloroethane as described above gave an additional 0.7 g of 2,5-dipicryl-1,3,4-oxadiazole (I) raising the total yield of I to 3.6 g (51%).

Recent scaled-up preparations of 2,5-dipicryl-1,3,4oxadiazole gave better yields than the small scale preparation of Example 2.

EXAMPLE 3

2,5-Dipicryl-1,3,4-oxadiazole (scaled up)

The N,N'-bis(2,4,6-trinitrobenzoyl)hydrazine starting material used for this example was obtained from Chemtronics, Inc., Swannanoa, N.C. This material contained 10 percent of a byproduct, methyl trinitrobenzoate, but a small scale test experiment indicated that this byproduct did not interfere with the preparation or purification of the 2,5-dipicryl-1,3,4 oxadiazole.

The large scale preparation of 2,5-dipicryl-1,3,4-oxadiazole was as follows: 125 g of the impure N,N'-bis(2,4,6-trinitrobenzoyl)hydrazine (corresponding to 112.5 g of pure material) was stirred in one liter of dry 1,2-dichloroethane in a 3-neck 2-liter round bottom flask (a mechanical stirrer was used). Phosphorus pentachloride (125 g) was added and the mixture was stirred at reflux temperature for 2.5 hours. After cooling to room temperature, the mixture was filtered to give 52.2 g of crude 2,5-dipicryl-1,3,4-oxadiazole. NMR of the crude product shows only 2,5-dipicryl-1,3,4-oxadiazole with a very small amount of N,N'-bis(trinitrobenzoyl)hydrazine.

The dichloroethane filtrate was stirred while 300 ml of cold water was added all at once. A precipitate immediately formed and the temperature of the mixture began to slowly rise. When the temperature reached 65°–70° C., small amounts of ice were added to hold the mixture at this temperature. After a short time the temperature began to fall and when the mixture was near room temperature, it was filtered to give 30.3 g of recovered bis(2,4,6-trinitrobenzoyl)hydrazine. Based on recovered starting material, the yield of crude 2,5-dipicryl-1,3,4oxadiazole was 66%. The yield of purified product by crystallization from acetone - methanol (as described in the small scale preparation of Example 2) was approximately 60%.

The crude 2,5-dipicryl-1,3,4-oxadiazole can also be purified by dissolving it in gamma-butyrolactone (1 gram per 5 ml of butyrolactone at 100° C.), treating the solution with charcoal, filtering and adding methanol to the filtrate to precipitate the product.

To those skilled in the art many modifications and variations of the present invention are possible in light of the above teachings. It is therefore to be understood that the present invention can be practiced otherwise than as specifically described herein and still be within the spirit and scope of the appended claims.

What is claimed and desired to be secured by Letters Patent of the United States is:

1. A process for preparing 2,5-dipicryl-1,3,4-oxadiazole comprising:
    (a) forming a reaction mixture of N,N'-bis(2,4,6-trinitrobenzoyl)hydrazine, phosphorus pentachloride, and a chlorinated hydrocarbon selected from the group consisting of 1,2-dichloroethane, 1,1,1-trichloroethane, 1,1,2trichloroethane, 1,1,2-trichloroethylene, and mixtures thereof;
    (b) heating the reaction mixture at a temperature of from 70° C. to the reflux temperature of the chlorinated hydrocarbon solvent until the N,N'-bis(2,4,6-trinitrobenzoyl)hydrazine has been converted to 2,5-dipicryl-1,3,4-oxadiazole; and
    (c) isolating the product 2,5-dipicryl-1,3,4-oxadiazole.

2. The process of claim 1 wherein the chlorinated hydrocarbon is 1,2-dichloroethane.

3. The process of claim 1 wherein step (b) is performed at reflux temperature for 2 or more hours.

4. The process of claim 1 wherein the molar ratio of phosphorous pentachloride to N,N'-bis(2,4,6-trinitrobenzoyl)hydrazine is from 1.0:1.0 to 3.0:1.0.

5. The process of claim 4 wherein the molar ratio of phosphorus pentachloride to N,N'-bis(2,4,6-trinitrobenzoyl)hydrazine is from 2.0:1.0 to 2.5:1.0.

6. The process of claim 1 wherein the reaction mixture is continuously agitated during step (b).

* * * * *